United States Patent
Pfeiffer et al.

(10) Patent No.: US 6,406,280 B1
(45) Date of Patent: Jun. 18, 2002

(54) DRIVE MOTOR FOR SURGICAL APPARATUS

(75) Inventors: Rolf Pfeiffer, Amberg; Gerd Zinn, Freudenberg; Rainer Haeusler, Tuttlingen, all of (DE)

(73) Assignees: Aesculap AG & Co. KG, Tuttlingen; Deprag Schulz GmbH u. Co., Amberg, both of (DE)

(*) Notice: Subject to any disclaimer, the term of this patent is extended or adjusted under 35 U.S.C. 154(b) by 0 days.

(21) Appl. No.: 09/638,277

(22) Filed: Aug. 14, 2000

Related U.S. Application Data

(63) Continuation of application No. PCT/EP98/00918, filed on Feb. 18, 1998.

(51) Int. Cl.[7] ............................. F01C 1/18; F01C 13/02
(52) U.S. Cl. ..................... 418/70; 418/152; 418/206.1; 418/206.9
(58) Field of Search ...................... 418/70, 152, 181, 418/206.1, 206.9, 270

(56) References Cited

U.S. PATENT DOCUMENTS

| | | | |
|---|---|---|---|
| 4,278,410 A | * | 7/1981 | de Gaillard .................. 418/108 |
| 4,505,677 A | | 3/1985 | Nakayama et al. .......... 433/132 |
| 4,566,849 A | | 1/1986 | Flink ............................ 415/92 |
| 5,219,174 A | * | 6/1993 | Zurbrugg et al. .............. 279/82 |
| 5,425,989 A | | 6/1995 | Ogaqa et al. ................ 428/333 |
| 5,546,824 A | | 8/1996 | Miller et al. ............... 74/421 R |
| 6,012,349 A | * | 1/2000 | Kelley ....................... 74/421 R |

FOREIGN PATENT DOCUMENTS

| | | |
|---|---|---|
| DE | 33 15 307 | 10/1984 |
| DE | 39 34 992 | 5/1991 |

OTHER PUBLICATIONS

*Patent Abstracts of Japan*, Abstract of Japanese Patent No. 05 172212, "Molded Gear", vol. 17, No. 592 (M–1502), Oct. 28, 1993.

* cited by examiner

*Primary Examiner*—John J. Vrablik
(74) *Attorney, Agent, or Firm*—Barry R. Lipsitz

(57) ABSTRACT

In order to achieve high rotational speeds for a drive motor used for surgical purposes without the need for excessive maintenance of this motor, it is proposed that it be in the form of a compressed-fluid-driven, gear-type motor having interengaging gears which are sealed in a housing and have a rotational speed of between 40,000 and 150,000 revolutions per minute.

17 Claims, 2 Drawing Sheets

DRIVE MOTOR FOR SURGICAL APPARATUS

Figure 1:
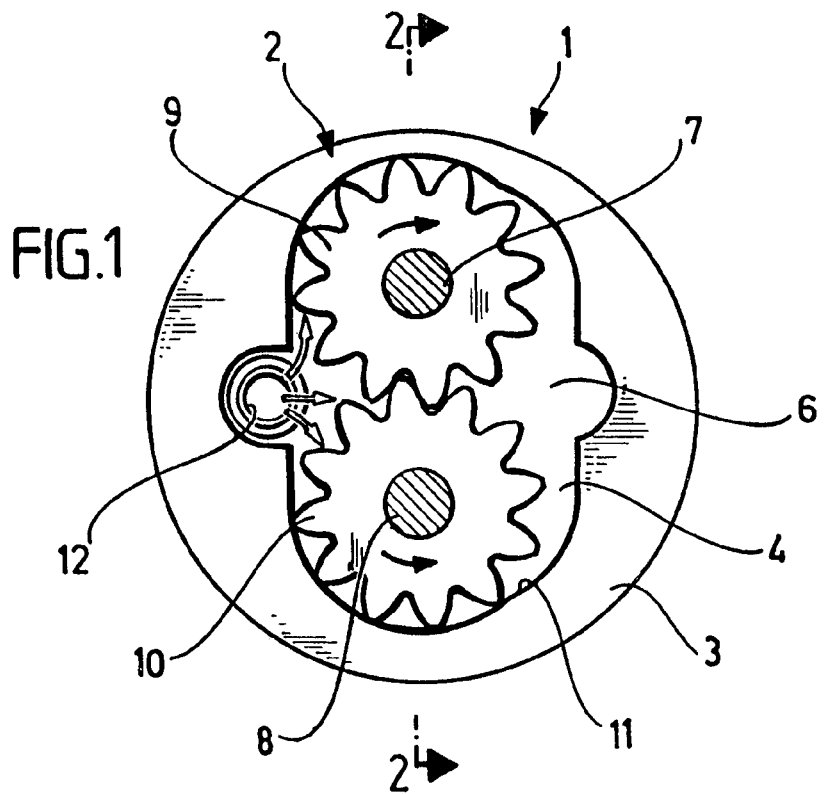

This application is a continuation of international application number PCT/EP98/00918 filed on Feb. 18, 1998.

The present invention relates to the subject matter disclosed in international application PCT/EP 98/00918 of Feb. 18, 1998, the entire specification of which is incorporated herein by reference.

The invention relates to a drive motor for surgical apparatus, for example, for dental tool holders, for bone drills or bone cutters.

In surgical apparatus of this type, it is necessary to drive the tools at high rotational speeds and, insofar as possible, the drive means should be operable by the energy sources available in a hospital, for example, compressed air.

In known surgical apparatus for example, turbine motors or rotary piston motors driven by compressed air are employed, these having the disadvantage however that they are relatively prone to wear and have to be intensively maintained by means of painstaking lubrication for example.

The object of the invention is to propose a suitable drive motor for use especially with surgical apparatus, whereby said motor can be driven at high rotational speeds together with the tool, and the motor can also function reliably without the need for intensive maintenance.

In accordance with the invention, this object is achieved in the case of a drive motor of the type described hereinabove in that it is a fluid-driven, gear-type motor incorporating interengaging gears which are sealed in a housing and have a rotational speed of between 40,000 and 150,000 revolutions per minute.

Surprisingly, it has been discovered that in contrast to fluid-driven turbine motors or rotary piston motors, fluid-driven gear-type motors are substantially better suited to employment in surgical apparatus. These motors are of very simple construction and merely comprise interengaging gears which are sealed on all sides in an encompassing housing together with a pressurised fluid supply conduit and a pressurised fluid outlet conduit, other moveable parts not being required, especially not radially displaceable disks such as are used in a rotary piston motor. This very simplified form of construction permits very high rotational speeds to be obtained and thereby the levels of performance to be attained such as are needed for employment in a surgical motor, for example, powers in the order of magnitude of 70 watts and upwards when using conventional pressures which may lie in a range of between 4 and 10 bar for example. There are scarcely any mutually rubbing parts in this new form of construction so that the necessity for lubrication is thereby reduced although the motor can nevertheless be driven at high rotational speeds without extensive maintenance being required.

The driving fluid may be a gas, for example, compressed air or nitrogen.

It is particularly advantageous for the gears of the gear-type motor to consist of a self-lubricating material, in particular, of polyoxymethylene (POM) or polyetheretherketone (PEEK). These self-lubricating materials permit operation to continue for particularly long periods of time and, moreover, it has been established that noise generation is relatively low when using such types of material so that the exhaust noises produced by the pressurised fluid emerging from the apparatus will remain within tolerable bounds.

It is advantageous for the outer diameter of the individual gears to be less than 40 mm. The diameter to width ratio of the gears may lie between 0.5 and 2.

The number of teeth on the gears should amount to at least 8. It is expedient if the modulus of the gears lies between 0.5 and 1.5.

This arrangement thereby results in a very compact constructional unit which requires very little space when employed in surgical apparatus and which, moreover, does not change the weight ratios of such an apparatus to a disadvantageous degree. This is of especial significance in the case of hand-held apparatus since the surgeon can then work for long periods of time with such types of hand-held apparatus without becoming unduly fatigued.

It is expedient if the bearing shaft of one of the gears of the gear-type motor is extended out from the housing of the gear-type motor in sealed manner and if it is coupled to a rotary tool without the intermediary of a reduction gear. The constructional outlay is also considerably reduced thereby, gear boxes can be completely dispensed with and the bearing shaft of the gear can be used directly as the drive shaft for the tool.

A particularly advantageous construction of a surgical apparatus is obtained when the housing of the gear-type motor is insertable into the tool holder of the surgical apparatus in a direction corresponding to that of the bearing shafts of the gears and is releasably fixed therein. The apparatus can then be easily dismantled, it sufficing to merely withdraw the motor out of the tool holder so that the tool holder can then be cleaned and sterilised in a conventional manner.

Figure 2:
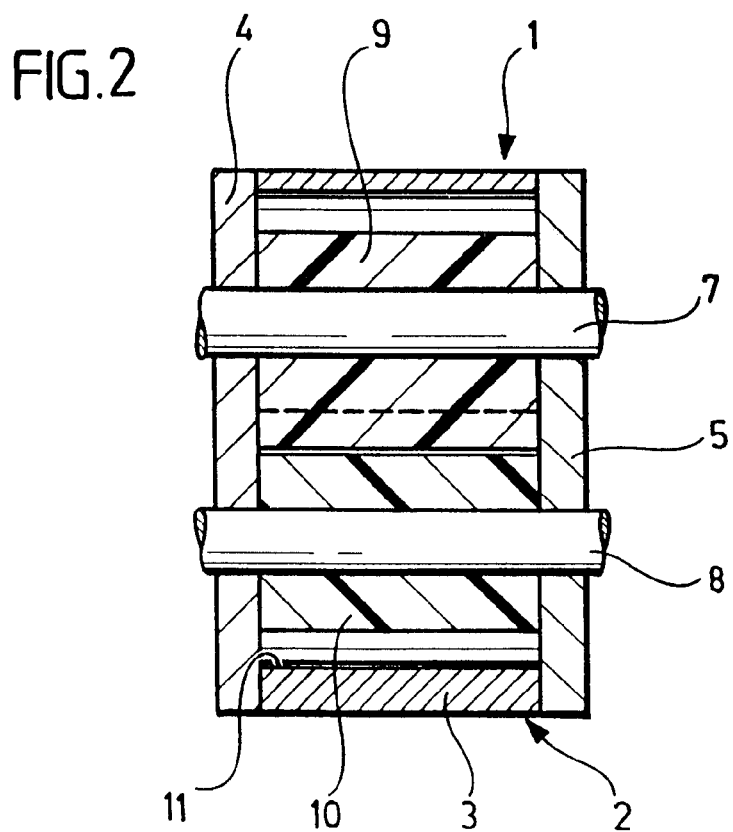

The following description of preferred embodiments of the invention will serve for providing a detailed explanation when taken in conjunction with the drawing. Therein FIG. 1 shows a sectional view through a gear-type motor for use in a surgical apparatus;

FIG. 2 a sectional view along the line 2—2 in FIG. 1 and

Figure 3:
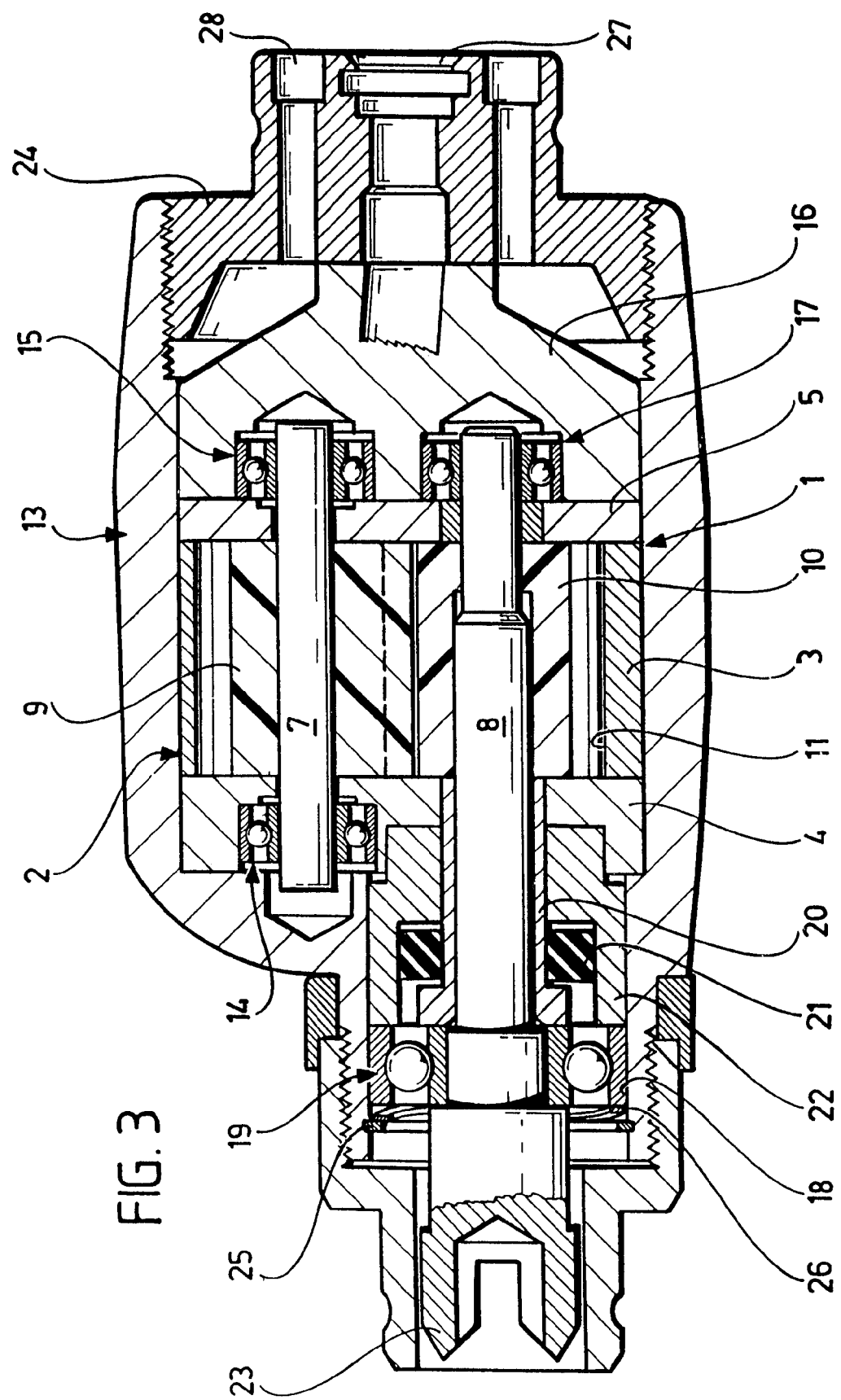

FIG. 3 a longitudinal sectional view of a surgical apparatus having a gear-type motor inserted therein.

The gear-type motor 1 schematically illustrated in FIGS. 1 and 2 comprises a closed housing 2 formed by a ring 3 and two flat end plates 4, 5 located on the end faces of the ring. Two mutually parallel bearing shafts 7, 8 are rotatably mounted between the two end plates 4, 5 across the interior 6 of the housing 2, each said bearing shaft carrying a respective gear 9 and 10 which is fixed thereon. The two gears extend over the whole width of the interior 6 and interengage at their outer peripheries. The shape of the interior 6 is selected to be such that the inner wall 11 of the ring 3 at the upper and lower ends of the interior 6 i.e. at the points remote from the point of engagement of the gears 9, 10, borders the outer peripheries of the gears 9, 10 in a manner such as to form a very narrow gap.

An inlet 12 enters the interior 6 at one side thereof in the spandrel between the two interengaging gears 9, 10, whilst an outlet from the interior 6 emerges at the opposite side of the interior 6 although this is not illustrated in the drawing.

The part of the interior 6 adjoining the inlet 12 is, to a large extent, sealed relative to the part of the interior 6 adjoining the outlet by virtue of the fact that, in the vicinity of the inner wall 11, the two gears 9, 10 are moved past it in a manner such as to form a very small gap, moreover, that they extend sideways such as to leave a very narrow gap relative to the flat end plates 4, 5, and finally, that the flanks of their teeth abut very closely together at their points of engagement. The compressed air, at a pressure of 6 bar for example, entering through the inlet thus impinges on the flanks of the teeth of the two gears 9, 10 in the spandrel adjacent the point of engagement of the gears 9, 10 and thereby exerts a torque on the two gears. The effective surfaces are thereby different for the differing directions of rotation since, in one direction of rotation, pressure is applied to a full flank of each gear whereas, in the other direction of rotation, pressure is applied to only one flank face in the region of engagement of the flanks of the teeth. As a consequence, the gears 9, 10 rotate in opposite senses when compressed air is applied thereto as indicated by the direction of the arrows shown in FIG. 1. The compressed air is carried along in the space between the flanks of the teeth and escapes through the outlet into the surroundings after it has been reduced in pressure.

The gears 9, 10, which one could also refer to as toothed rollers, preferably have an outer diameter of less than 40 mm. The diameter to width ratio of the gear D/B preferably lies between 0.5 and 2, whilst the number of teeth amounts to at least 8. The modulus of the gears lies between 0.5 and 1.5.

The toothing on the gears may be straight or bevelled, whilst it is expedient if the gears 9, 10 consist of a self-lubricating material, for example, of polyoxymethylene (POM) or polyetheretherketone (PEEK).

A gear-type motor, such as is schematically illustrated in FIGS. 1 and 2, is illustrated in FIG. 3 in a housing 13 of a surgical apparatus although, in the embodiment illustrated, only the housing 13 of a tool holder of this surgical apparatus is illustrated without the supply arrangements and without a tool.

It can be perceived in the gear-type motor 1 of this embodiment that a bearing shaft 7 is mounted at each end in ball bearings 14, 15, one of these being disposed in one of the end plates 4 and the other in a terminating portion 16 directly adjoining the end plate 5.

The other bearing shaft 8 is likewise mounted in the terminating portion 16 by means of a ball bearing 17, but this shaft extends through the end plate 4 of the gear-type motor 1 into a cylindrical extension 18 of the housing 13 of the tool holder and is mounted therein by means of a ball bearing 19 which is somewhat distanced from the gear-type motor 1. The bearing shaft 8 is surrounded by a sleeve 20 in the region between the end plate 4 and the ball bearing 19, said sleeve being sealed relative to a sleeve-shaped insert 22 in the cylindrical extension 18 by means of an O-ring seal 21.

The free end of the bearing shaft 8 carries a coupling 23 in which a tool can be mounted in known manner by means of a chuck for example although this is not visible in the drawing. This tool may be a burr, a drill or a similar rotary tool.

The gear-type motor 1 can be withdrawn backwardly out of the open end of the housing 13 together with the bearing shaft 8 and the parts surrounding it i.e. the ball bearing 19, the sleeve 20, the seal 21 and the insert 22. This can be done after a plate-like closure member 24 has been unscrewed from the open end of the housing 13.

Conversely, the gear-type motor 1 can be reinserted into the housing 13 in a similar manner whereby the ball bearing 19 abuts against an annular shoulder 25 within the cylindrical extension 18 as the motor is pushed in, a resiliently compressible locking washer 26 possibly being provided as an intermediary. The requisite pressure in the direction towards the annular shoulder 25 is produced by the closure member 24 which abuts the rear end of the terminating portion 16 and pushes the gear-type motor 1 forward longitudinally of the housing 13 when it is screwed into the housing 13.

A central compressed air conduit 27 and a plurality of air extraction conduits 28 are disposed in the closure member 24. The compressed air conduit is connected to the inlet 12 although this is not visible in the drawing whilst the air extraction conduits 28 are in communication in the terminating portion 16 with the outlet from the interior 6 although this too is not visible in the drawing.

Thus, the gear-type motor 1 can be constructed in the form of a very compact independent module so that it is possible to remove it from the surgical apparatus in a simple manner for the purposes of cleaning and sterilisation for example. It is also readily possible to replace this motor by another motor having different operational properties when differing operational parameters are desired for alternative purposes.

In the embodiment of a gear-type motor illustrated in the drawing, the two gears 9 and 10 are rotatably mounted in the housing 2 by means of the bearing shafts 7 and 8, whereby, for their part, the bearing shafts 7, 8 are rigidly connected to the gears 9 and 10.

In a modified embodiment, it would also be possible for just the bearing shaft 8 to be rotatably mounted in this manner, said shaft then being rigidly connected to the appertaining gear 10. The other gear 9 could be mounted in freely rotatable manner on the bearing shaft 7 which, for its part, would then be mounted in non-rotational manner in the housing 2 as a fixed axle.

What is claimed is:

1. A surgical apparatus including a tool holder in the form of a housing and a fluid-driven drive motor disposed in said tool holder, wherein the drive motor is a gear-type motor incorporating interengaging gears which are sealed in a housing and are fixedly mounted on bearing shafts which are rotatably mounted in the housing of the gear-type motor and have a rotational speed of between 40,000 and 150,000 revolutions per minute, and the housing of the gear-type motor is inserted into the housing of the tool holder of the surgical apparatus in a direction corresponding to that of the bearing shafts of the gears and is releasably fixed therein.

2. An apparatus in accordance with claim 1, wherein the operating pressure of the fluid used for driving the drive motor lies between 4 and 10 bar.

3. An apparatus in accordance with claim 1, wherein the outer diameter of the gears (9, 10) is less than 40 mm.

4. An apparatus in accordance with claim 1, wherein the diameter to width ratio of the gears (9, 10) lies between 0.5 and 2.

5. An apparatus in accordance with claim 1, wherein the number of teeth on the gears (9, 10) amounts to at least 8.

6. An apparatus in accordance with claim 1, wherein the modulus of the gears (9, 10) lies between 0.5 and 1.5.

7. An apparatus in accordance with claim 1, wherein the bearing shaft (8) of one of the gears (10) of the gear-type motor (1) is extended out from the housing (2) of the gear-type motor (1) in sealed manner and is coupled to a rotary tool without the intermediary of a reduction gear.

8. An apparatus in accordance with claim 1, wherein the driving fluid is a gas.

9. An apparatus in accordance with claim 8, wherein the driving fluid is compressed air or nitrogen.

10. An apparatus in accordance with claim 1, wherein the gears (9, 10) of the gear-type motor (1) consist of a self-lubricating material.

11. An apparatus in accordance with claim 10, the gears (9, 10) of the gear-type motor (1) consist of polyoxymethylene (POM).

12. An apparatus in accordance with claim 10, the gears (9, 10) of the gear-type motor (1) consist of polyetheretherketone (PEEK).

13. An apparatus in accordance with claim 10, wherein the modulus of the gears (9, 10) lies between 0.5 and 1.5.

14. An apparatus in accordance with claim 10, wherein the outer diameter of the gears (9, 10) is less than 40 mm.

15. An apparatus in accordance with claim 14, wherein the diameter to width ratio of the gears (9, 10) lies between 0.5 and 2.

16. An apparatus in accordance with claim 10, wherein the diameter to width ratio of the gears (9, 10) lies between 0.5 and 2.

17. An apparatus in accordance with claim 16, wherein the modulus of the gears (9, 10) lies between 0.5 and 1.5.

* * * * *